United States Patent [19]

Anderson et al.

[11] Patent Number: 5,264,546

[45] Date of Patent: Nov. 23, 1993

[54] COPOLYMER PRODUCTION

[75] Inventors: Alistair J. Anderson, Hull; Edwin A. Dawes, Humberside; Geoffrey W. Haywood, Hull; David Byrom, Cleveland, all of England

[73] Assignee: Imperial Chemical Industries PLC, London, England

[21] Appl. No.: 870,480

[22] Filed: Apr. 17, 1992

Related U.S. Application Data

[62] Division of Ser. No. 517,654, May 1, 1990, Pat. No. 5,126,255.

[30] Foreign Application Priority Data

May 2, 1989 [GB] United Kingdom ............... 8909993
Oct. 4, 1989 [GB] United Kingdom ............... 8922363

[51] Int. Cl.$^5$ .................... C08G 63/06; C12P 7/62
[52] U.S. Cl. ................... 528/361; 528/354; 435/135; 435/822; 435/829; 435/843; 435/872
[58] Field of Search ........... 435/135, 822, 829, 872, 435/843; 528/361, 354

[56] References Cited

U.S. PATENT DOCUMENTS

| | | | |
|---|---|---|---|
| 4,997,909 | 3/1991 | Doi | 435/135 |
| 5,126,255 | 6/1992 | Anderson et al. | 435/135 |

FOREIGN PATENT DOCUMENTS

| | | | |
|---|---|---|---|
| 114086 | 7/1984 | European Pat. Off. | |
| 204442 | 5/1986 | European Pat. Off. | |
| 288908 | 11/1988 | European Pat. Off. | 435/135 |
| 304293 | 2/1989 | European Pat. Off. | 435/135 |

OTHER PUBLICATIONS

Marchessault et al., "Physical Properties of Poly-$\beta$-hydroxyvalerate: A Natural Chiral Polyalkanoate", IUPAC Macro Florence 1980 International Symposium on Macromolecules Preprints 2 (1980), pp. 272-275.

*Primary Examiner*—Herbert J. Lilling
*Attorney, Agent, or Firm*—Cushman, Darby & Cushman

[57] ABSTRACT

A process for the synthesis of copolymers comprising 3-hydroxybutyrate (HB) and 3-hydroxyvalerate (HV) units by the cultivation of certain strains of Corynebacterium, and Rhodococcus, some of which are novel on a substrate containing e.g. glucose. The process can also be used to produce the previously unknown homopolymer of HV by using a substrate of valeric acid.

4 Claims, No Drawings

COPYMER PRODUCTION

This application is a divisional of Ser. No. 07/517,654 filed May 1, 1990, now U.S. Pat. No. 5,126,255.

This invention relates to a process for producing copolymers of 3-hydroxybutyrate monomer units and 3-hydroxyvalerate monomer units, hereinafter referred to as HB, and HV respectively, and to a microorganism for use in such a process.

Homopolymer of HB, known as polyhydroxybutyrate and hereinafter referred to as PHB, is accumulated by various microorganisms, principally bacteria, as an energy reserve material as granules within the microbial cells. The analogous homopolymer of HV, PHV has not hitherto been isolated.

PHB extracted from such cells is a thermoplastic polyester of the repeat structure

—O.CH(CH$_3$).CH$_2$.CO— that crystallises to a relatively high level e.g. of the order of 70% or more. This crystallisation behaviour is often disadvantageous when PHB is to be used as, for example, a moulding material.

It is known that the crystallisation of PHB may be modified by incorporation of units of a dissimilar monomer into the polymer chain. It is also known that by cultivation of the microorganism under certain conditions in the presence of certain acids, and alcohols, a proportion of comonomer units may be introduced into the polymer chain, so as to produce a copolymer.

The term comonomer is herein used to denote those monomer units present in the copolymer that are not HB monomer units.

The term copolymer is herein used to denote those copolymers comprising comonomer units and HB monomer units.

Although we do not wish to be bound by the following theory, it is thought that the metabolic pathway leading to such copolymers is as follows, in which CoA.SH is unesterified Coenzyme A,
CH$_3$.CO.S.CoA is the acetyl thioester of Coenzyme A and is more commonly termed acetyl CoA,
NADP is nicotinamide adenine dinucleotide phosphate in the oxidised state, and
NADPH$_2$ is reduced NADP.

It is believed that, in the biosynthesis of PHB by a microorganism, the first step is the synthesis of acetyl CoA. This can be formed for example, from CoA and acetate, or by the oxidative decarboxylation of pyruvate, which is the product of the metabolisation of carbohydrates, or which can be formed by decarboxylation of oxaloacetate, the latter being a member of the tricarboxylic acid (TCA) cycle, otherwise known as the Krebs cycle.

Thus with acetate as the source of acetyl CoA, the PHB is produced by a metabolic pathway involving the reactions:

1. CH$_3$.CO.O$^-$ + CoA.SH — thickinase → CH$_3$.CO.S.CoA + OH$^-$
2. 2CH$_3$.CO.S.CoA — B ketothiolase → CH$_3$.CO.CH$_2$.CO.S.CoA + CoA.SH
3. CH$_3$.CO.CH$_2$.CO.S.CoA — reductase → CH$_3$.CHOH.CH$_2$.CO.S.CoA + NADP +NADPH$_2$
4. CH$_3$.CHOH.CH$_2$.CO.S.CoA — polymerase → O.CH(CH$_3$).CH$_2$.CO— + CoA.SH wherein
CH$_3$.CO.CH$_2$.CO.S.CoA is acetoacetyl CoA,
CH$_3$.CHOH.CH$_2$.CO.S.CoA is 3-hydroxybutyryl CoA and
—O.CH(CH$_3$).CH$_2$.CO— is a repeat unit in the polymer.

Thus reaction 4 adds —O.CH(CH$_3$).CH$_2$.CO— to a growing polymer chain.

Because of a lack of specificity of the enzymes involved, the corresponding pathway with, for example propionic acid, is thought to be:

1a. CH$_3$.CH$_2$.CO.O$^-$ + CoA.SH — thickinase → CH$_3$.CH$_2$.CO.S.CoA + OH$^-$
2a. CH$_3$.CH$_2$.CO.S.CoA — B ketothiolase → CH$_3$.CH$_2$.CO.CH$_2$.CO.S.CoA + CoA.SH + CH$_3$.CO.S.CoA
3a. NADPH$_2$ + — reductase → NADP + CH$_3$.CH$_2$.CHOH.CH$_2$.CO.S.CoA CH$_3$.CH$_2$.CO.CH$_2$.CO.S.CoA
4a. CH$_3$.CH$_2$.CHOH.CH$_2$.CO.S.CoA — polymerase →—O.CH(C$_2$H$_5$).CH$_2$.CO— + CoA.SH wherein
CH$_3$.CH$_2$.CO.S.CoA is propionyl CoA,
CH$_3$.CH$_2$.CO.CH$_2$.CO.S.CoA is 3-ketovaleryl CoA,
CH$_3$.CH$_2$.CHOH.CH$_2$.CO.S.CoA is 3-hydroxyvaleryl CoA and
—O.CH(C$_2$H$_5$).CH$_2$.CO— is a repeat unit in the polymer.

Thus reaction 4a adds —O.CH(C$_2$H$_5$).CH$_2$.CO— to a growing polymer chain.

Certain copolymers containing HB monomer units together with various comonomer units have been described in the literature together with processes for obtaining these copolymers.

Thus copolymers exhibiting an infra-red band said to be indicative of ethylenic unsaturation are described by Davis in "Applied Microbiology" 12 (1964) pages 301 to 304. These copolymers which are said by Davis to be copolymers containing HB monomer units and 3-hydroxy-2-butenoate comonomer units, i.e. comonomer units of the formula

—O.C(CH$_3$)=CH.CO— were prepared by cultivating Nocardia on n-butane.

Also Wallen et al describe in "Environmental Science and Technology" 6 (1972) pages 161 to 164 and 8 (1974) pages 576 to 579 a copolymer melting at 97° to 100° C. (after repeated washing) isolated from activated sludges and containing HB monomer units and HV comonomer units, in the ratio of 1:5. The copolymer thus contains about 17% of HB monomer units.

Marchessault et al reported in "IUPAC Macro Florence 1980 International Symposium on Macromolecules Preprints" 2 (1980) pages 272 to 275 a study of this copolymer and confirmed that it contained mainly HV comonomer units.

U.S. Pat. No. 3,275,610 describes the microbiological production of polyesters by cultivating certain microorganisms, especially *Nocardia salmonicolor*, on carboxylic acids containing 4 carbon atoms.

EP-B-0052459 and EP-B-69497 describe the microbiological production of a number of polyesters by cultivating certain microorganisms especially *Alcaligenes eutrophus* mutant NCIB 11599 on suitable substrates. (The abbreviations NCIB and NCIMB herein refer to the National Collections of Industrial and Marine Bacteria Ltd., 23 St. Machar Drive, Aberdeen AB2 1RY, United Kingdom). It is stated that certain carbon containing compounds are not suitable for inclusion in the substrate, as the microorganisms are not able to synthesise and accumulate comonomer units from these particular carbon containing compounds. These carbon containing compounds include formic, acetic, succinic and lactic acids, and also glucose. It is shown that the microorganisms are able to grow on glucose, and that when cultivated under polymer and copolymer accumulating conditions on a substrate in which the carbon containing compound consists of glucose, only PHB is produced and accumulated.

Similarly, EP-A-204442 describes the microbiological production of copolymers of HB and HV by the cultivation of *Alcaligenes eutrophus* mutant NCIB 12080 on primary alcohols having an odd number of carbon atoms, but excluding methanol.

Doi et al in Applied Microbiology and Biotechnology, 28 (1988), pp 330–334, have shown that when *Alcaligenes eutrophus* ATCC 17699 and *Alcaligenes eutrophus* NCIB 11599 are cultivated on a substrate in which the carbon containing compound consisted of glucose, acetic acid or butyric acid, only PHB was produced and accumulated. Furthermore, Doi et al also show that in order for a microorganism to produce and accumulate copolymer, the substrate must contain a carbon containing compound having a structure comparable with that of the comonomer.

When PHB-accumulating bacteria are aerobically cultured in a medium comprising a suitable substrate, which contains a source of energy and carbon, they reproduce until one or more of the essential requirements for reproduction is exhausted. This reproduction of the bacteria is hereinafter referred to as growth. Upon exhaustion of an essential growth requirement, further growth occurs only to a very limited extent, if at all, but, providing the substrate is not exhausted, PHB may be accumulated by the bacteria.

With some bacteria, even in the absence of a PHB-inducing constraint such as a limitation of one or more of the essential growth requirements, PHB may also be accumulated while growth of the bacteria is taking place: however, except in the case of bacteria that produce PHB constitutively, the amount of PHB so accumulated is generally small and typically is less than 10% by weight of the cells produced. Thus when grown in batch culture, the bacteria that do not produce PHB constitutively, will grow, with little or no PHB accumulation, until one or more of the essential requirements for growth becomes exhausted, and then the bacteria synthesise PHB.

In order to produce copolymers it is necessary to provide a substrate comprising a component that is capable of giving rise to the comonomer units during at least part of the period when copolymer is accumulated. Thus, as hereinbefore described, in order to produce a copolymer of HB monomer units and HV comonomer units the bacteria are required to be cultivated on a substrate comprising a component from which HV comonomer units are capable of being synthesised.

The component that gives rise to at least the HV comonomer units within the copolymer is herein termed the HV component of the substrate.

Conventionally such HV components excluded sugars such as glucose, and acids such as formic, acetic, butyric, lactic and succinic, or any carbon source that could preferentially be metabolised by the bacteria, even under growth limitation conditions, by pathways leading to e.g. acetyl CoA, or to a member of the TCA cycle, and thereby essentially restricting the bacteria to the production of PHB.

We have found that certain selected strains of bacteria may be cultivated under polymer accumulating conditions so as to produce a copolymer comprising HB monomer units, and HV comonomer units, wherein the substrate comprises an assimilable carbon compound, and that the assimilable carbon compound is one that is metabolisable to PHB alone by known PHB-accumulating bacteria.

We have also found that it is possible to provide a general microbiological process for the production of such copolymers which utilises the selected bacteria.

We have further found that the HV comonomer content may be so varied that in effect the PHV homopolymer may be produced.

Accordingly, we provide a process for the synthesis of copolymers comprising HB monomer units and HV comonomer units characterised in that said process comprises aerobically cultivating a bacterium having the characteristics of at least one bacterium selected from the group consisting of *Corynebacterium dioxydans* ATCC 21766, *Corynebacterium hydrocarboxydans* ATCC 21767, *Norcardia lucida* NCIB 10980, Rhodococcus sp. ATCC 19070 and Rhodococcus sp. NCIMB 40126 under growth limitation conditions in an aqueous medium comprising a substrate, said substrate comprising an HV component, wherein the HV component is an assimilable carbon compound that is metabolisable by *Alcaligenes eutrophus* NCIB 11599 to PHB. (The abbreviation ATCC herein refers to the American Type Culture Collection, 12301 Parklawn Drive, Rockville, Md. 20852, United States of America).

Depending on the conditions of cultivation employed, e.g. the HV component, strain of bacteria, the number of HV comonomer units in the copolymer may be varied. Usually the number of HV comonomer units in the copolymer is at least 5 mol %, preferably at least 50 mol %, particularly between 60 and 98 mol %, and is especially between 70 and 95 mol % of the total number of HB monomer units and HV comonomer units in the copolymer. Under certain cultivation conditions, e.g. when the HV component is valeric acid, or a derivative thereof, there may be no HB monomer units detected, in which case the copolymer is effectively an HV homopolymer, which has not hitherto been available.

Furthermore, by including in the substrate an other comonomer component, the copolymer produced may also contain comonomers, other than HV comonomers. Specifically, the inclusion of 4-hydroxybutyrate, hexanoic acid, or 5-chlorovaleric acid in the substrate leads to the inclusion of comonomers of 4-hydroxybutyrate, 3-hydroxyhexanoate, and 5-hydroxyvalerate comonomers in the copolymer.

Preferably the process utilises at least one strain of bacteria selected from strain *Corynebacterium dioxydans*

ATCC 21766, *Corynebacterium hydrocarboxydans* ATCC 21767, *Norcardia lucida* NCIB 10980, Rhodococcus sp. ATCC 19070 and Rhodococcus sp. NCIMB 40126, in particular the process utilises strain Rhodococcus sp. NCIMB 40126.

Other strains of bacteria, having similar characteristics to the aforementioned preferred strains, may be used in the process of the present invention. The other strains may inherently have these desired characteristics, or may have acquired these desired characteristics through transference of the necessary genetic information from strains which possess the desired characteristics. The transference of the genetic information, required for the production and accumulation of PHB, between strains of bacteria has previously been disclosed by Schubert et al in the Journal of Bacteriology, 12 (1988) pages 5837 to 5847, and by Slater et al also in the Journal of Bacteriology, 10 (1988) pages 4431 to 4436.

The concentration of the HV component in the aqueous medium is preferably between 0.1 and 25, particularly between 5 and 10 $g.1^{-1}$.

The HV component may be a sugar such as glucose, or fructose, or a salt, ester, anhydride, amide, halide of acetic, lactic, butyric or succinic acid, or derivatives thereof.

Mixtures of compounds suitable for use as HV components may be used, such as those found in molasses, or derivatives thereof.

In addition to the carbon containing substrate and oxygen, various nutrients are required for growth of the bacteria. These nutrients comprise the following elements, which are normally present in readily assimilable form, normally as water soluble salts: nitrogen, phosphorus, sulphur, potassium, sodium, magnesium, calcium, and iron, together with traces of manganese, zinc and copper.

It is preferred that at least part of the cultivation is conducted under conditions of limitation of an essential requirement for growth but not copolymer accumulation. In particular it is preferred to restrict the supply of one or more of the nutrients. The most practical elements to limit are nitrogen, phosphorus, or, less preferably, magnesium, sulphur or potassium. The nitrogen may be conveniently supplied in the form of an ammonium salt, whereas the phosphorus may be conveniently supplied as a phosphate.

Where nitrogen limitation is employed, the substrate is preferably nitrogen free and so amide derivatives of those acids capable for use as HV components are less preferred HV components. The amount of assimilable nitrogen required is about 10 to 15% by weight of the desired weight of cells less the weight of the accumulated copolymer.

Cultivation of the bacteria may be conducted under conditions of temperature, pH, degree of aeration etc. conventionally used for the bacteria under non-growth limiting conditions. Likewise the amounts of nutrients (other than that of the nutrient used to limit the growth of the bacteria) employed may be those normally provided for growth of the bacteria.

Cultivation of the bacteria preferably comprises a two stage process. In the first stage the bacteria are preferably grown to a certain dry weight per liter, under non-growth limiting conditions on a substrate comprising a readily assimilable carbon compound, for example glucose. In the second stage the substrate is at least in part the HV component, and at least one nutrient required for growth is limited, such that the growth limiting conditions exist.

The cultivation may be performed as a batch process, such that polymer accumulation will occur as the amount of the nutrient required for growth but not polymer accumulation becomes depleted.

Alternatively, the cultivation may be performed as a continuous process, wherein a stream of culture is removed from the vessel, in which the bacteria is being cultivated, on a continuous or semi continuous basis. The stream removed from the vessel contains bacterial cells in a spent aqueous medium. The spent aqueous medium comprises residual quantities of nutrients and substrate. The flowrate of the stream leaving the vessel corresponds to the rate of addition of fresh aqueous medium to the vessel. The fresh aqueous medium supplied to the vessel contains nutrients and substrate in sufficient amounts to support accumulation of the copolymer. Preferably the amount of that nutrient, used to limit the growth of the bacteria, which is fed to the vessel is such that little or none of that nutrient is present in the spent aqueous medium removed from the vessel. Further, it is preferred that the spent aqueous medium is fed to at least one further aerated cultivation stage under batch or preferably continuous or semi-continuous operation, wherein additional copolymer accumulation is stimulated by the addition of fresh HV component containing substrate to the spent aqueous medium. The levels of nutrients and substrate may be adjusted in the spent aqueous medium after leaving the first cultivation stage such that optimum operation of the overall process is maintained.

Alternatively, the cultivation of the bacteria may be conducted as a single stage process. In such a process, wherein copolymer accumulation is induced by limiting the amount of a nutrient required for growth but not for copolymer accumulation, the residence time of the aqueous medium in the vessel is made sufficiently long so as to allow exhaustion of the limiting nutrient, and for copolymer accumulation to occur.

In either a single or multistage process, or in a batch or semi continuous or continuous process the HV component may be present as the sole source of carbon present in the substrate during copolymer accumulation, or may be in admixture with other assimilable carbon sources.

The HV component may be present in the substrate for only part of the copolymer accumulation stage.

According to a further aspect of the invention we provide a pure culture of a Rhodococcus sp. strain designated NCIMB 40126, and mutants and variants derived therefrom.

The strain Rhodococcus sp. NCIMB 40126 was deposited on the Mar. 24, 1989, under the terms and conditions of the Budapest Treaty.

The strain Rhodococcus sp. NCIMB 40126 and useful mutants and variants derived therefrom may be characterised by the following taxonomic description, in which the ability of the strain, and mutants and variants derived therefrom, to grow on a substrate consisting of glucose, in conjunction with an ability to accumulate a copolymer comprising HB monomer units and HV comonomer units under polymer accumulating conditions using glucose as the assimilable carbon source, are distinguishing features.

Description of Rhodococcus sp. NCIMB 40126

Morphology

Gram positive non-motile rods of approximate size 0.6 to 1.2 μm by 3.0 to 9.5 μm.
No spore formation.
Branching of cells and coccoid forms noted.
Colonial morphology (Lab M Nutrient Agar)—the organism is in the form of circular, smooth, entire, pale pink to orange colonies.
Growth exhibited at pH from 5 to 9.
Temperature
Optimum temperature 30° to 35° C.

| Characteristics | |
|---|---|
| Acid From | |
| Glucose | + |
| Fructose | + |
| Mannitol | + |
| Xylose | − |
| Lactose | − |
| Sucrose | − |
| Starch | − |
| Maltose | − |
| Galactose | − |
| Mannose | − |
| Arabinose | − |
| Cellulose | − |
| Growth on Sole Carbon Sources | |
| Lactate | + |
| Succinate | + |
| Fructose | + |
| Glucose | + |
| Citrate | + |
| Acetate | + |
| Sucrose | − |
| Xylose | − |
| Lactose | − |
| Glycerol | − |
| Others | |
| Catalase | + |
| $NO_3^-$ to $NO_2^-$ | − |
| Gelatin stability | No Gelatin Liquefaction |
| Litmus milk | Alkaline |
| BCP Milk | Alkaline |
| Indole | |
| $H_2S$ | + |
| Methyl red | − |
| Acetylmethyl Carbinol | − |
| $NH_3$ | − |

The process of the present invention is illustrated by the following examples.

EXAMPLE 1

A starter culture of Rhodococcus sp. NCIMB 40126 was grown in Brain Heart Infusion (Oxoid), hereinafter termed BHI.

1 ml of the starter culture was used to inoculate 200 ml of KR medium.

The KR medium had the following composition, per liter of distilled water:

| | |
|---|---|
| $MgSO_4.7H_2O$ | 0.4 (g) |
| $FeSO_4.7H_2O$ | 0.025 (g) |
| $(NH_4)_2SO_4$ | 7.0 (g) |
| $K_2HPO_4$ | 7.6 (g) |
| $NaH_2PO_4$ | 6.24 (g) |
| Trace solution | 10.0 (ml) |
| Glucose | 10.0 (g) |

The trace solution had the following composition, per liter of distilled water:

| | |
|---|---|
| $MnSO_4.4H_2O$ | 0.406 (g) |
| $ZnSO_4.7H_2O$ | 0.440 (g) |
| $CuSO_4.5H_2O$ | 0.078 (g) |
| $CaCl_2.2H_2O$ | 7.340 (g) |

The bacterium was grown in aerobic (shake-flask) batch culture at pH 7.0, and 30° C. for 24 hours.

After 24 hours the bacteria were harvested by centrifugation, washed, and transferred to a further 200 ml of KR medium which contained no ammonium sulphate.

The bacterium was cultivated for a further 24 hours so as to allow for polymer accumulation. The bacterium was then harvested by centrifugation, washed, freeze dried and the polymer content was determined by gas chromatography of the methyl 3-hydroxy acids produced by methanolysis of the whole bacteria.

Analysis showed there to be a total of 12.8% w/w of copolymer present, of which 70 mol % was HV comonomer units.

Two repeat experiments were conducted, maintaining glucose as the carbon compound. Copolymer was produced in each case. In one instance 22.8% w/w of copolymer was produced, in the other 21% w/w. The amount of HV comonomer units present in each instance were 80 mol % and 75 mol % respectively.

EXAMPLE 2

Example 1 was repeated except that molasses was used as the assimilable carbon compound instead of glucose, at the same weight per liter of KR medium.

Analysis of the copolymers produced showed there to be 4.3% w/w of copolymer present, of which 59 mol % was HV comonomer units.

EXAMPLE 3

Example 1 was repeated except that sodium acetate was used as the assimilable carbon compound instead of glucose, at the same weight per liter of KR medium.

Analysis of the copolymers produced showed there to be 25.0% w/w of copolymer present, of which 70 mol % was HV comonomer units.

EXAMPLE 4

Example 1 was repeated except that sodium lactate was used as the assimilable carbon compound instead of glucose, at the same weight per liter of KR medium.

Analysis of the copolymers produced showed there to be 11.2% w/w of copolymer present, of which 80 mol % was HV comonomer units.

EXAMPLE 5

Example 1 was repeated except that sodium succinate was used as the assimilable carbon compound instead of glucose, at the same weight per liter of KR medium.

Analysis of the copolymers produced showed there to be 4.1% w/w of copolymer present, of which 92 mol % was HV comonomer units.

EXAMPLE 6

Example 1 was repeated except that fructose was used as the assimilable carbon compound instead of glucose, at the same weight per liter of KR medium.

Analysis of the copolymers produced showed there to be 12.4% w/w of copolymer present, of which 80 mol % was HV comonomer units.

EXAMPLE 7

Example 1 was repeated except that *Corynebacterium dioxydans* ATCC 21766 was used instead of Rhodococcus sp. NCIMB 40126.

Analysis of the copolymers produced showed there to be 12.8% w/w of copolymer present, of which 70 mol % was HV comonomer units.

EXAMPLE 8

Example 1 was repeated except that Rhodococcus sp. ATCC 19070 was used instead of Rhodococcus sp. NCIMB 40126.

Analysis of the copolymers produced showed there to be 14.3% w/w of copolymer present, of which 90 mol % was HV comonomer units.

EXAMPLE 9

Example 3 was repeated except that *Nocardia lucida* NCIB 10980 was used instead of Rhodococcus sp. NCIMB 40126.

Analysis of the copolymers produced showed there to be 19.8% w/w of copolymer present, of which 49 mol % was HV comonomer units.

EXAMPLE 10

Example 3 was repeated except that *Corynebacterium hydrocarboxydans* ATCC 21767 was used instead of Rhodococcus sp. NCIMB 40126.

Analysis of the copolymers produced showed there to be 21.1% w/w of copolymer present, of which 42 mol % was HV comonomer units.

EXAMPLE 11

The capacity of Rhodococcus sp. NCIMB 40126 to produce and accumulate a polymer containing HV comonomer when cultivated on a substrate wherein the assimilable carbon compound is a conventional HV component was confirmed by repeating Example 1, except that during the growth limiting stage the glucose was replaced by valeric acid.

Analysis of the copolymers produced showed there to be 53.0% w/w of copolymer present, of which 98 mol % was HV comonomer units.

EXAMPLE 12

The capacity of Rhodococcus sp. NCIMB 40126 to produce and accumulate a polymer containing a comonomer other than a HV comonomer, when cultivated on a substrate wherein the assimilable carbon compound is glucose and a component capable of being utilised to provide the non-HV comonomer, was confirmed by repeating Example 1, except that during the growth limiting stage the glucose was supplemented by sodium 4-hydroxybutyrate (1 g.l$^{-1}$).

Analysis of the copolymers produced showed there to be 16.6% w/w of copolymer present, of which 63 mol % was HV comonomer units, and 13 mol % was 4-hydroxybutyrate comonomer units.

EXAMPLE 13

Example 12 was repeated except that hexanoic acid replaced the sodium 4-hydroxybutyrate (1 g.l$^{-1}$).

Analysis of the copolymers produced showed there to be 21.4% w/w of copolymer present, of which 44 mol % was HV comonomer units, and 17 mol % was 3-hydroxyhexanoate comonomer units.

EXAMPLE 14

Example 12 was repeated except that 5-chlorovaleric acid replaced the sodium 4-hydroxybutyrate (1 g.l$^{-1}$).

Analysis of the copolymers produced showed there to be 25.0% w/w of copolymer present, of which 59 mol % was HV comonomer units, and 10 mol % was 5-hydroxyvalerate comonomer units.

EXAMPLE 15

A starter culture of Rhodococcus sp. NCIMB 40126 was grown in Nutrient Broth (Oxoid), hereinafter termed NB.

6 ml of the starter culture was used to inoculate 600 ml of NB medium, and the bacterium was grown in aerobic (shake-flask) culture at 30° C. for 24 hours.

After 24 hours the bacteria were harvested as described in Example 1, and transferred to nitrogen-free KR medium (pH 7.0) containing valeric acid (5 g.l$^{-1}$) as the sole carbon source. After a further 24 hours incubation, with shaking at 30° C. the bacteria were harvested and analysed as for Example 1.

Analysis of the polymer produced showed there to be 60% w/w of polymer present, with no detectable presence of HB monomer units, i.e. the polymer was effectively HV homopolymer.

This example is similar to that of Example 11. The main difference between these examples is that in Example 11 the bacterium was able to accumulate a small proportion of PHB during the first stage of the process when grown on glucose under non-growth limiting conditions, whereas in the present example no such glucose was present during the initial stages of the process.

The following table summarises the results of Examples 1 to 15.

| Example No. | Polymer % w/w | Monomers % mol | | |
|---|---|---|---|---|
| | | HB | HV | Others |
| 1a | 12.8 | 30 | 70 | — |
| 1b | 23.0 | 20 | 80 | — |
| 1c | 21.0 | 25 | 75 | — |
| 2 | 4.3 | 41 | 59 | — |
| 3 | 25.0 | 30 | 70 | — |
| 4 | 11.2 | 20 | 80 | — |
| 5 | 4.1 | 8 | 92 | — |
| 6 | 12.4 | 20 | 80 | — |
| 7 | 12.8 | 30 | 70 | — |
| 8 | 14.3 | 10 | 90 | — |
| 9 | 19.8 | 51 | 49 | — |
| 10 | 21.1 | 58 | 42 | — |
| 11 | 53.0 | 2 | 98 | — |
| 12 | 16.6 | 24 | 63 | — |
| 13 | 21.4 | 39 | 44 | 17 |
| 14 | 25.0 | 31 | 69 | 10 |
| 15 | 60.0 | 0 | 100 | — |

In a number of comparative experiments a number of other strains of Corynebacterium were examined for potential growth on glucose, and accumulation of copolymer. The strains examined were unable to grow on glucose, consequently cultivation of the strains was initially established on BHI, and thereafter they were transferred to a substrate containing glucose under non-growth conditions.

| Strain | Growth | Polymer |
|---|---|---|
| *Corynebacterium sp.* ATCC 21744 | None | None |

-continued

| Strain | Growth | Polymer |
| --- | --- | --- |
| Corynebacterium sp. ATCC 21745 | None | PHB |
| Corynebacterium sp. ATCC 21746 | None | PHB |
| Corynebacterium sp. ATCC 21747 | None | None |
| Corynebacterium equi | None | None |

We claim:

1. A homopolymer of PHV consists of 3-hydroxyvalerate (HV) monomer units.

2. A process for the synthesis of PHV homopolymer which consists of 3-hydroxyvalerate (HV) monomer units, said process comprising aerobically cultivating a bacterium selected from the group consisting of *Corynebacterium dioxydans* ATCC 21766, *Corynebacterium hydrocarboxydans* ATCC 21767, *Norcardia lucida* NCIB 10980, Rhosoxoxxua sp. ATCC 19070 and *Rhodococcus* sp. NCIMB 40126 under growth limitation conditions in an aqueous medium comprising a substrate, said substrate comprising an HV component, wherein the HV component is valeric acid or a derivative thereof.

3. A process as claimed in claim 2 wherein the bacterium is selected from the group consisting of *Corynebacterium dioxydans* ATCC 21766, *Corynebacterium hydrocarboxydans* ATCC 21767, *Norcardia lucida* NCIB 10980, *Rhodococcus* sp. ATCC 19070, *Rhodococcus* sp. NCIMB 40126.

4. A process as claimed in claim 2 wherein the bacterium is *Rhodococcus* sp. NCIMB 40126.

* * * * *